United States Patent
Sanchez-Sotelo et al.

(10) Patent No.: US 11,058,544 B2
(45) Date of Patent: Jul. 13, 2021

(54) MINIMALLY INVASIVE SHOULDER IMPLANT AND METHOD

(71) Applicant: Howmedica Osteonics Corp., Mahwah, NJ (US)

(72) Inventors: Joaquin Sanchez-Sotelo, Rochester, MN (US); David Viscardi, Glen Rock, NJ (US)

(73) Assignee: Howmedica Osteonics Corp., Mahwah, NJ (US)

( * ) Notice: Subject to any disclaimer, the term of this patent is extended or adjusted under 35 U.S.C. 154(b) by 0 days.

(21) Appl. No.: 16/593,116

(22) Filed: Oct. 4, 2019

(65) Prior Publication Data
US 2020/0129300 A1    Apr. 30, 2020

Related U.S. Application Data

(60) Provisional application No. 62/750,914, filed on Oct. 26, 2018.

(51) Int. Cl.
*A61F 2/40* (2006.01)
*A61B 17/00* (2006.01)
(Continued)

(52) U.S. Cl.
CPC ...... *A61F 2/4014* (2013.01); *A61B 17/00234* (2013.01); *A61F 2/30749* (2013.01);
(Continued)

(58) Field of Classification Search
CPC ........ A61F 2/4014; A61F 2/40; A61F 2/4003; A61F 2/36; A61F 2/3601; A61F 2/3603;
(Continued)

(56) References Cited

U.S. PATENT DOCUMENTS

| 6,102,953 A | 8/2000 | Huebner |
| 8,157,866 B2 * | 4/2012 | Winslow ............... A61F 2/4014 |
| | | 623/19.14 |

(Continued)

FOREIGN PATENT DOCUMENTS

IT    201600080874 A1    2/2018

OTHER PUBLICATIONS

Extended European Search Report for Application No. EP19204700.9, dated Apr. 7, 2020, pp. 1-3.

*Primary Examiner* — Jennifer Dieterle
*Assistant Examiner* — Amanda M Barkan
(74) *Attorney, Agent, or Firm* — Lerner, David, Littenberg, Krumholz & Mentlik, LLP (57) ABSTRACT

A method of implanting a prosthetic stemless shoulder implant may include making an incision into a patient's shoulder area of a patient and passing a cutting instrument through a rotator cuff interval of the patient. A central portion of the native humeral head may be resected and removed so that a central void remains. The same or another cutting instrument may be inserted through the rotator cuff interval and into the central void. Medial and lateral portions of the native humeral head adjacent the central void may be resected and removed. A base of a prosthesis may be implanted into a proximal portion of the humerus after passing the base through the rotator cuff interval, and two humeral head portions may be inserted through the rotator cuff interval and coupled to the base and to one another.

16 Claims, 12 Drawing Sheets

(51) Int. Cl.
*A61F 2/30* (2006.01)
*A61F 2/46* (2006.01)
*A61B 17/16* (2006.01)

(52) U.S. Cl.
CPC ........ *A61F 2/4612* (2013.01); *A61B 17/1684* (2013.01); *A61B 2017/00238* (2013.01); *A61F 2002/30245* (2013.01); *A61F 2002/30357* (2013.01); *A61F 2002/4018* (2013.01); *A61F 2002/4632* (2013.01)

(58) Field of Classification Search
CPC ............ A61F 2/3609; A61F 2002/4018; A61F 2002/4022; A61F 2002/2853; A61F 2002/4007; A61F 2002/3611; A61F 17/00234; A61F 17/1684; A61F 17/1778; A61F 2017/564
See application file for complete search history.

(56) References Cited

U.S. PATENT DOCUMENTS

| | | | |
|---|---|---|---|
| 8,361,126 B2 * | 1/2013 | Perrow | A61B 17/8891 |
| | | | 606/287 |
| 8,689,425 B2 | 4/2014 | Mutchler et al. | |
| 10,368,999 B2 * | 8/2019 | Greiwe | A61B 17/15 |
| 2004/0167629 A1 | 8/2004 | Geremakis et al. | |
| 2012/0116530 A1 | 5/2012 | Forsell | |
| 2018/0271668 A1 | 9/2018 | Kemp et al. | |
| 2020/0352728 A1 * | 11/2020 | Hodorek | A61F 2/30749 |

* cited by examiner

FIG. 12 the extent of the page.

MINIMALLY INVASIVE SHOULDER IMPLANT AND METHOD

CROSS-REFERENCE TO RELATED APPLICATIONS

This application claims the benefit of the filing date of U.S. Provisional Patent Application No. 62/750,914, filed Oct. 26, 2018, the disclosure of which is hereby incorporated by reference herein.

FIELD OF THE DISCLOSURE

The present application generally relates to a minimally invasive shoulder prosthesis and a method of implantation of a shoulder prosthesis.

BACKGROUND OF THE DISCLOSURE

Over time and through repeated use, bones and joints can become damaged or worn. For example, repetitive strain on bones and joints (e.g., through athletic activity), traumatic events, and certain diseases (e.g., arthritis) can cause cartilage in joint areas, for example, which normally provides a cushioning effect, to wear down. When the cartilage wears down, fluid can accumulate in the joint areas, resulting in pain, stiffness, and decreased mobility. The same can happen in cases where tendons in a joint become lax or soft tissues in or adjacent the joint become damaged or worn.

Arthroplasty procedures can be used to repair such damaged joints. During a typical arthroplasty procedure, an arthritic or otherwise dysfunctional joint can be remodeled or realigned. A prosthesis or prostheses can be implanted to repair the damaged region(s). Arthroplasty procedures may take place in any of a number of different regions of the body, such as the knees, hips, shoulders, or elbows, for example. One type of arthroplasty procedure is a shoulder arthroplasty, in which a damaged shoulder joint may be replaced with prosthetic implants. The shoulder joint may have been damaged by, for example, arthritis (e.g., severe osteoarthritis or degenerative arthritis), trauma, or a destructive joint disease.

Prostheses that are implanted into a damaged region may provide support and structure to the damaged region, and may help to restore the damaged region, thereby enhancing its functionality. Prior to implantation of a prosthesis in a damaged region, the damaged region may be prepared to receive the prosthesis. In the case of a shoulder arthroplasty procedure, one or more of the bones in the shoulder area, such as the humerus and/or glenoid, may be treated (e.g., cut, drilled, reamed, and/or resurfaced) to provide one or more surfaces that can align with the implant and thereby accommodate the implant.

It is often preferable to create the fewest and/or smallest incisions practicable when implanting a prosthesis, while cutting or otherwise damaging the least amount of tissue possible. For example, during a traditional shoulder arthroplasty procedure, a large incision is typical and transection, followed by reattachment, of the subscapularis muscle is required. The large incision may lead to a correspondingly larger scar and a longer recovery time. Further, the transection and reattachment of the subscapularis muscle may increase likelihood of subscapularis failure following the arthroplasty.

BRIEF SUMMARY OF THE DISCLOSURE

According to one aspect of the disclosure, a method of implanting a prosthetic stemless shoulder implant includes making an incision into a shoulder area of a patient. A first cutting instrument may be inserted through the incision and through a rotator cuff interval of the patient. A central portion of a native humeral head of the patient may be resected with the first cutting instrument. The central portion of the native humeral head of the patient may be removed so that a central void remains where the central portion of the native humeral head was previously positioned. A second cutting instrument may be inserted through the incision, through the rotator cuff interval, and into the central void. Medial and lateral portions of the native humeral head adjacent the central void may be resected and removed. A base of a prosthetic stemless shoulder may be implanted into a proximal portion of the humerus after passing the base through the rotator cuff interval. A first portion of a prosthetic humeral head may be coupled to the base after passing the first portion of the prosthetic humeral head through the rotator cuff interval. A second portion of the prosthetic humeral head may be coupled to the base and to the first portion of the prosthetic humeral head after passing the second portion of the prosthetic humeral head through the rotator cuff interval.

The second cutting instrument may be the same as or different than the first cutting instrument. The prosthetic stemless shoulder implant may be implanted without transecting a subscapularis muscle of the patient. The prosthetic stemless shoulder implant may be implanted without transecting a supraspinatus muscle of the patient. Resecting the central portion of the native humeral head may include making a first cut in the native humeral head, making a second cut in the native humeral head, and making a third cut in the native humeral head connecting the first cut to the second cut. The first cut and the second cut may be substantially parallel to one another. The third cut may be substantially orthogonal to the first cut and to the second cut. Resecting the medial portion of the native humeral head may include making a fourth cut substantially parallel to the third cut. Resecting the lateral portion of the native humeral head may include making a fifth cut substantially parallel to the third cut. The first cutting instrument may be coupled to a robotic surgical system during resection of the central portion of the native humeral head. The first cutting instrument may be a manual cutting instrument.

The first portion of the prosthetic humeral head and the second portion of the prosthetic humeral head may form a substantially hemispherical shape when coupled together. The first portion of the prosthetic humeral head may form a substantially half-hemispherical shape, and the second portion of the prosthetic humeral head form a substantially half-hemispherical shape. A seam may be formed between the first portion of the prosthetic humeral head and the second portion of the prosthetic humeral head when the first portion of the prosthetic humeral head is coupled to the second portion of the prosthetic humeral head. The first portion of the prosthetic humeral head may have an outer surface with a substantially constant first radius of curvature and a region adjacent the seam having a second radius of curvature smaller than the first radius of curvature. The first portion of the prosthetic humeral head may be coupled to the base prior to coupling the second portion of the prosthetic humeral head to the first portion of the prosthetic humeral head.

According to another aspect of the disclosure, a prosthetic stemless shoulder implant includes a base including an anchor portion, a collar portion, and a coupling member. A prosthetic humeral head may have a first portion adapted to couple to the coupling member and a second portion adapted to couple to the coupling member and the first portion of the prosthetic humeral head. The prosthetic humeral head may be substantially hemispherically shaped when the first portion of the prosthetic humeral head is coupled to the second portion of the prosthetic humeral head. The first portion of the prosthetic humeral head may form a substantially half-hemispherical shape, and the second portion of the prosthetic humeral head may form a substantially half-hemispherical shape. A seam may be formed between the first portion of the prosthetic humeral head and the second portion of the prosthetic humeral head when the first portion of the prosthetic humeral head is coupled to the second portion of the prosthetic humeral head. The first portion of the prosthetic humeral head may have an outer surface with a substantially constant first radius of curvature and a region adjacent the seam having a second radius of curvature smaller than the first radius of curvature.

DETAILED DESCRIPTION

As used herein, the term "proximal" refers to a location closer to an individual's heart, and the term "distal" refers to a location farther away from the individual's heart. When used in the context of an implant, the terms "proximal" and "distal" refer to locations on the implant closer to, or farther away from, the heart when the implant is implanted in an intended manner. As used herein, the term "medial" refers to a location closer to the midline of an individual, while the term "lateral" refers to allocation farther away from the midline of the individual. Further, it should be understood that although the term "stemless implant" is used herein, the term does not indicate that a stemless implant fully lacks any anchor, but rather a stemless implant may include an anchor that is significantly smaller and/or shorter than stems of typical known stemmed implants.

Figure 1:
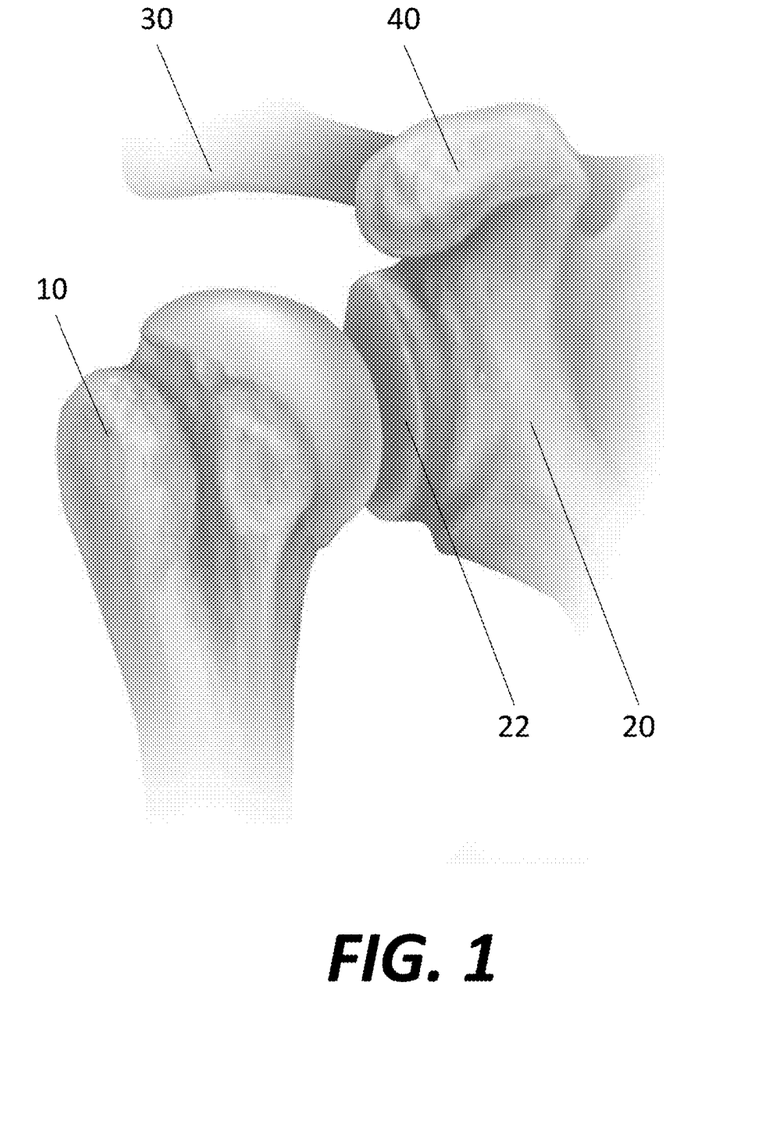
FIG. 1 is a view of bones of a shoulder joint.
Figure 2:
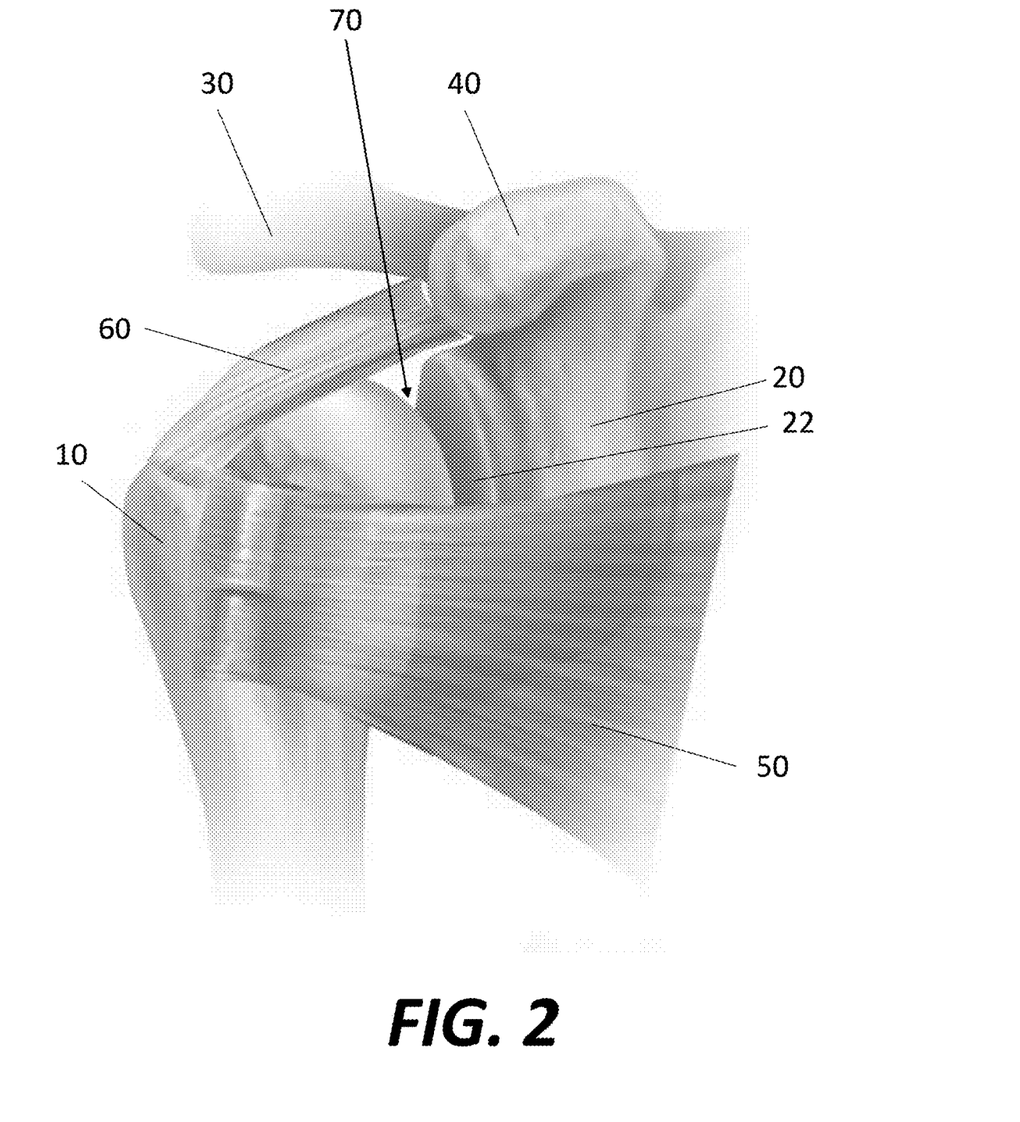
FIG. 2 is a view of the bones of the shoulder joint of FIG. 1 along with representations of the subscapularis muscle and the supraspinatus muscle.

FIG. 1 illustrates bones of a right shoulder joint as viewed anteriorly (from the front of a patient). Generally, the bones of the shoulder joint include humerus 10, a proximal end of which includes a head or ball of the ball-and-socket joint, and scapula 20, which includes the glenoid cavity 22 that forms the socket of the ball-and-socket joint. The acromion 30 and coracoid process 40 are also illustrated in FIG. 1. FIG. 2 illustrates the bones of FIG. 1 but also provides representations of the subscapularis muscle 50 and the supraspinatus muscle 60. Generally, the subscapularis muscle 50 is attached to the lesser tubercle of the humerus 10, and the supraspinatus muscle 60 is attached to the greater tubercle of the humerus 10. The subscapularis muscle 50 and supraspinatus muscle 60 form two of the four muscles forming the rotator cuff. As shown in FIG. 2, a generally triangular space is formed between (i) the tendons of the subscapularis muscle 50, (ii) the tendons of the supraspinatus muscle 60, and (iii) the base of the coracoid process 40. This triangular space is known as the rotator cuff interval 70, and as described in greater detail below, provides a space through which instruments may be inserted for a minimally invasive shoulder arthroplasty procedure. It should be understood that FIG. 2 is not intended to be a complete representation of all soft tissue pertinent in a shoulder joint.

Figure 3:
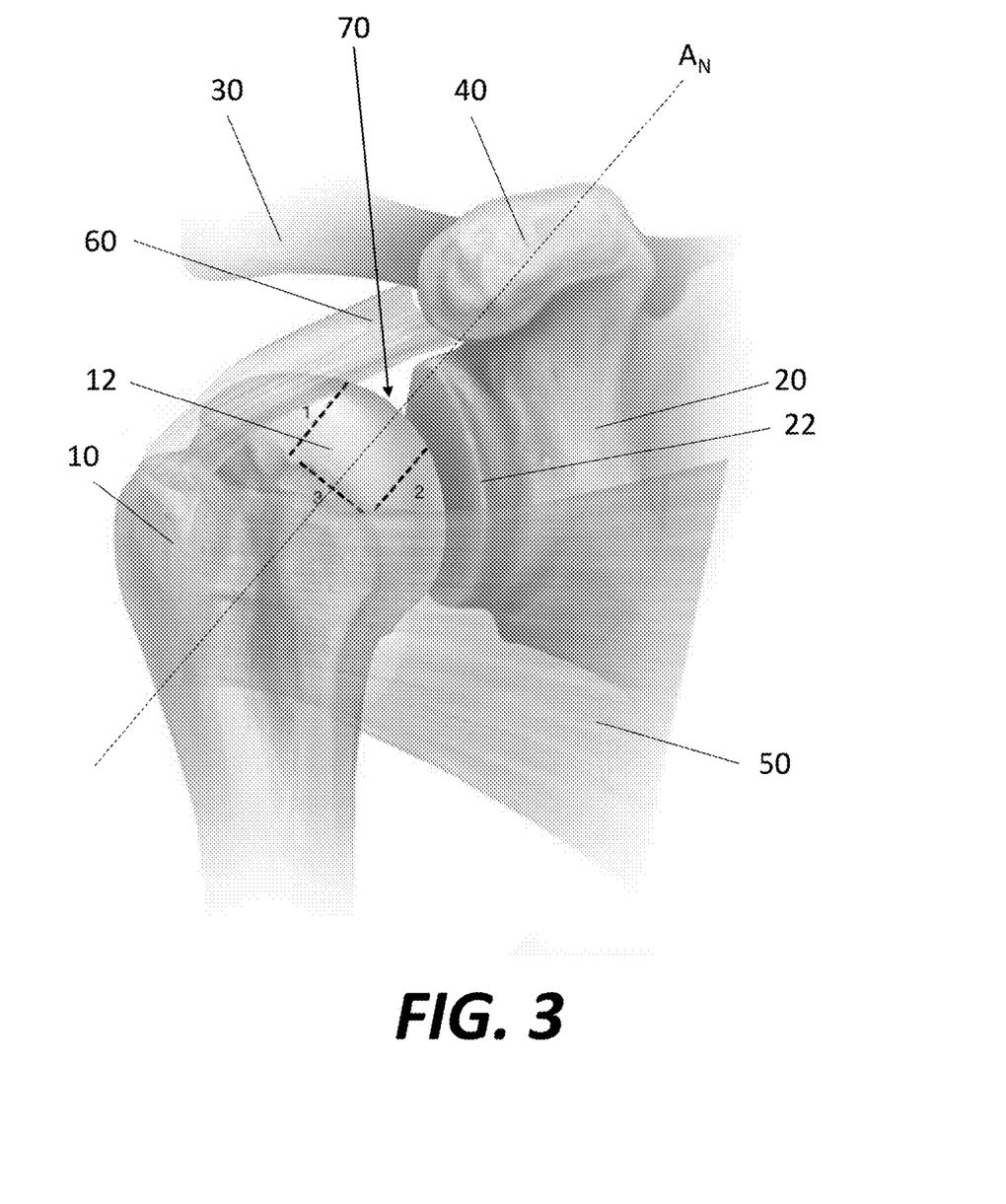
FIG. 3 illustrates the shoulder joint shown in FIG. 2, with the muscles being partially transparent and a first group of cut lines illustrated on the humeral head.

One aspect of a shoulder arthroplasty may include removal of the head of the humerus 10 and replacement of the humeral head with a prosthetic humeral head. As noted above, resection of the humeral head traditionally requires a large incision and transection of soft tissue such as the subscapularis muscle 50. However, in a method according to the present disclosure, a small incision may be made within a patient's shoulder to access the head of the humerus 10 through the rotator cuff interval 70. In one example, the incision may be performed as deltopectoral approach, which may be an anterior approach. However, it should be understood that alternate approaches, including a superior approach, may be suitable for use with the disclosure described herein. Further, although the procedure may be generally performed with only a single incision, additional incisions may be created during the procedure. For example, a second incision may be made to create a window below the subscapularis, with this second incision being used to remove posterior osteophytes and/or to perform other accessory methods, such as capsular release, including inferior capsular release. Other second incisions may also be made if desired, although generally the primary incision is the only incision needed for the actual joint replacement procedure, as discussed in greater detail below. With this small incision, a single cut to remove the head of the humerus 10 may be difficult or impossible, particularly if the goal is to achieve minimal unnecessary soft tissue damage. As shown in FIG. 3, once access to the rotator cuff interval 70 is established, a central segment 12 of the head of humerus 10 may be resected. In the illustrated example, a first cut 1, a second cut 2, and a third cut 3 are made to remove the central segment 12 of the head of the humerus 10. In particular, first cut 1 and second cut 2 may be substantially parallel to one another and substantially parallel to a central axis $A_N$ of the neck of the humerus 10. Third cut 3 may be substantially orthogonal to the first cut 1 and second cut 2 and may connect the first cut 1 to the second cut 2. Although three cuts are labeled in FIG. 3, it should be understood that more or fewer cuts may be suitable for removing the central segment 12 of the head of the humerus 10. Further, the first cut 1, second cut 2, and third cut 3 do not necessarily need to be performed in that order, although it may be easiest to complete the first cut 1 and second cut 2 prior to completing the resection of the central segment 12 of the head of the humerus 10 with the third cut 3.

Figure 4:
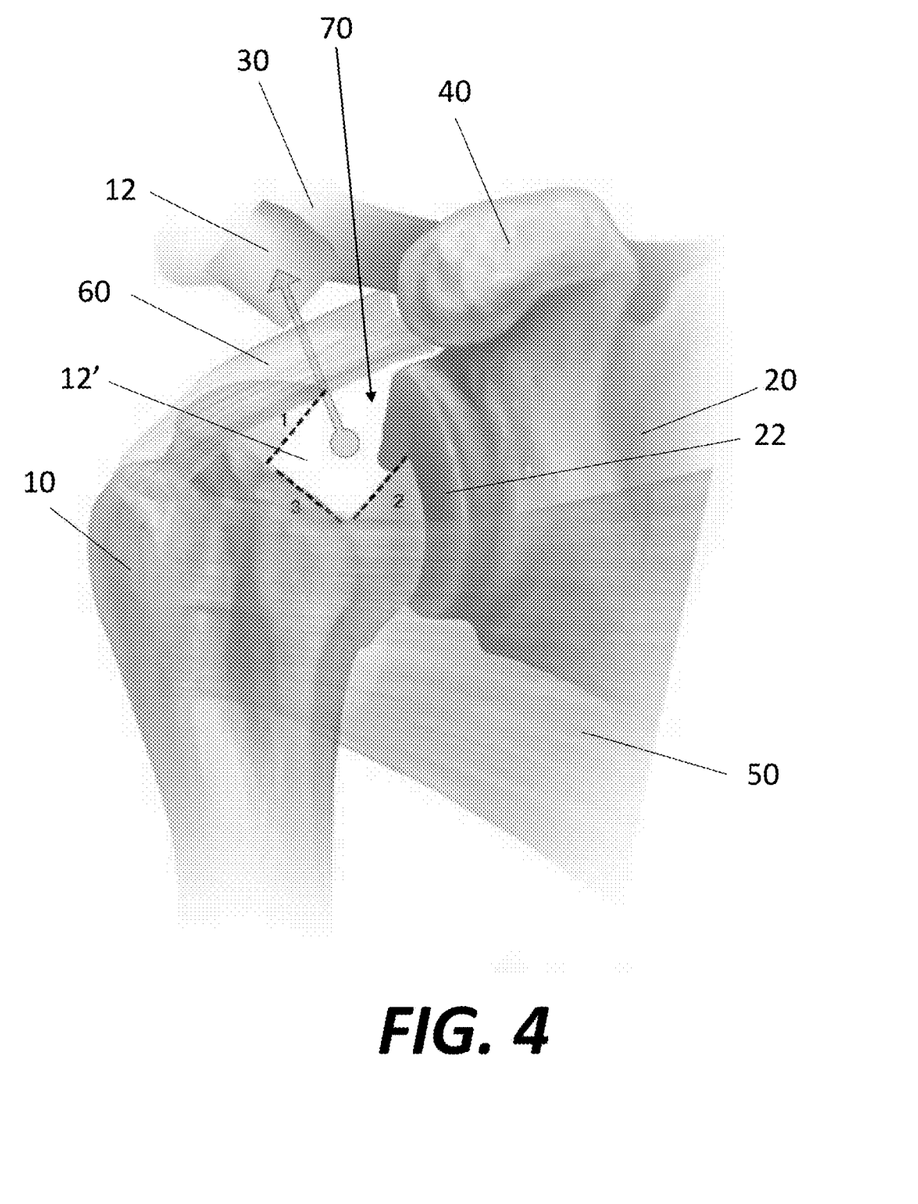
FIG. 4 is illustrates a portion of the humeral head of FIG. 3 being removed after cutting along the cut lines of FIG. 3.

After the cuts of the central segment 12 of the head of the humerus 10 are complete, the central segment 12 may be removed through the incision as shown in FIG. 4, leaving a central void 12' corresponding to the shape of central segment 12. After removal of the central segment 12, the corresponding void 12' may provide space that allows additional osteotomies to be performed under the subscapularis muscle 50 and supraspinatus muscle 60 (or otherwise under tendons connecting those muscles to humerus 10) and thus to minimize or avoid damage to those muscles and/or corresponding tendons.

Figure 5:
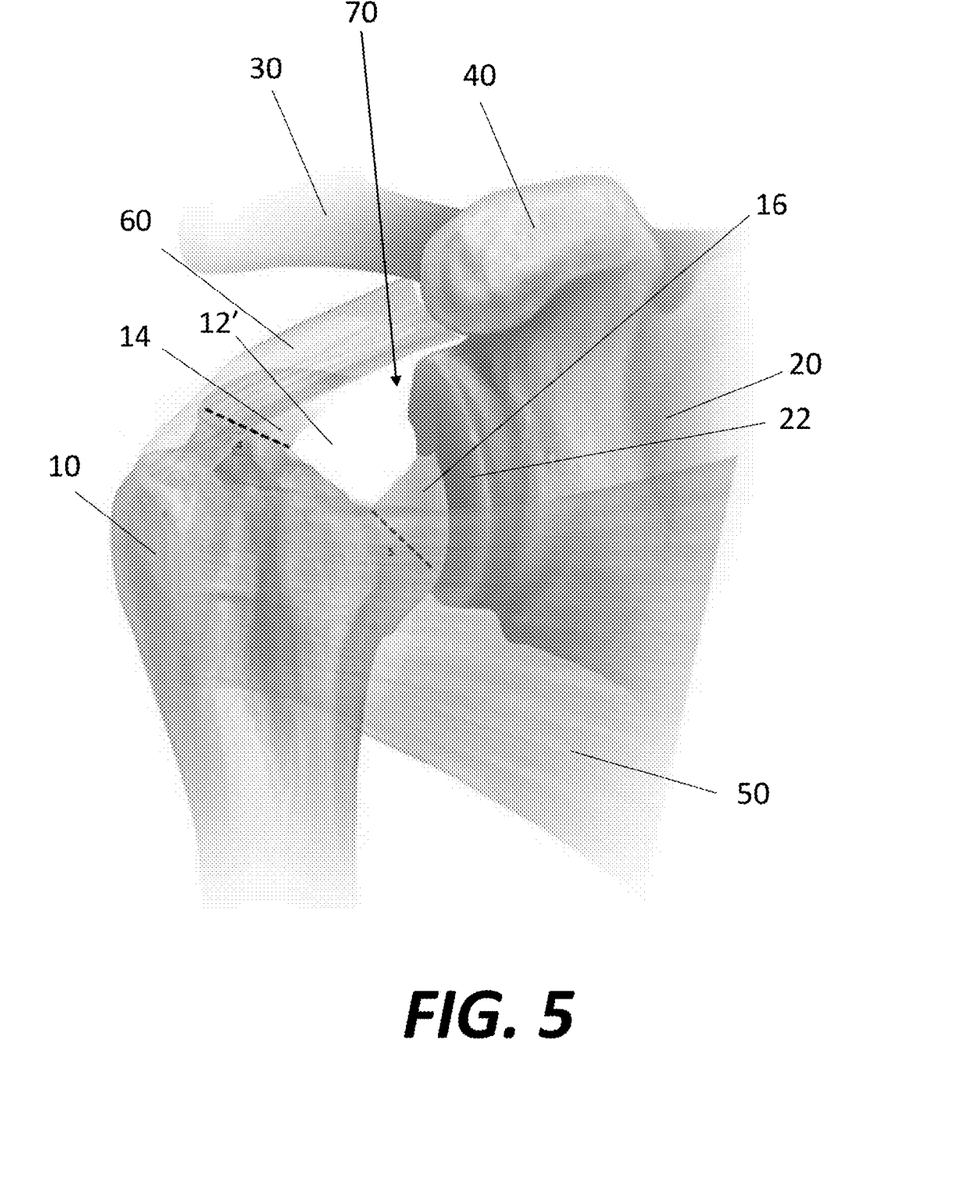
FIG. 5 is illustrates a second group of cut lines on the humeral head of FIG. 4.
Figure 6:
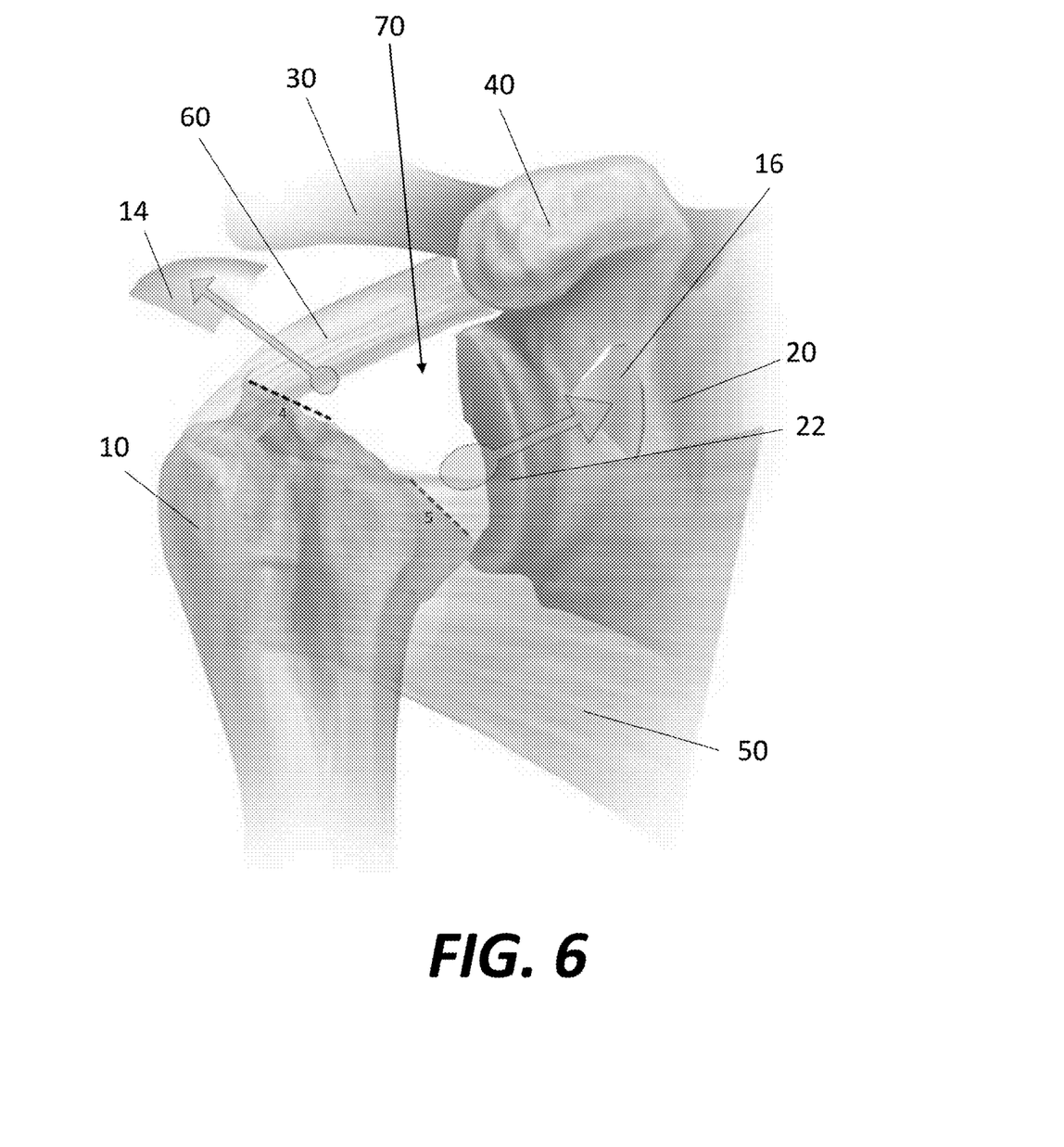
FIG. 6 illustrates two portions of the humeral head of FIG. 5 being removed after cutting along the cut liens of FIG. 5.
Figure 7:
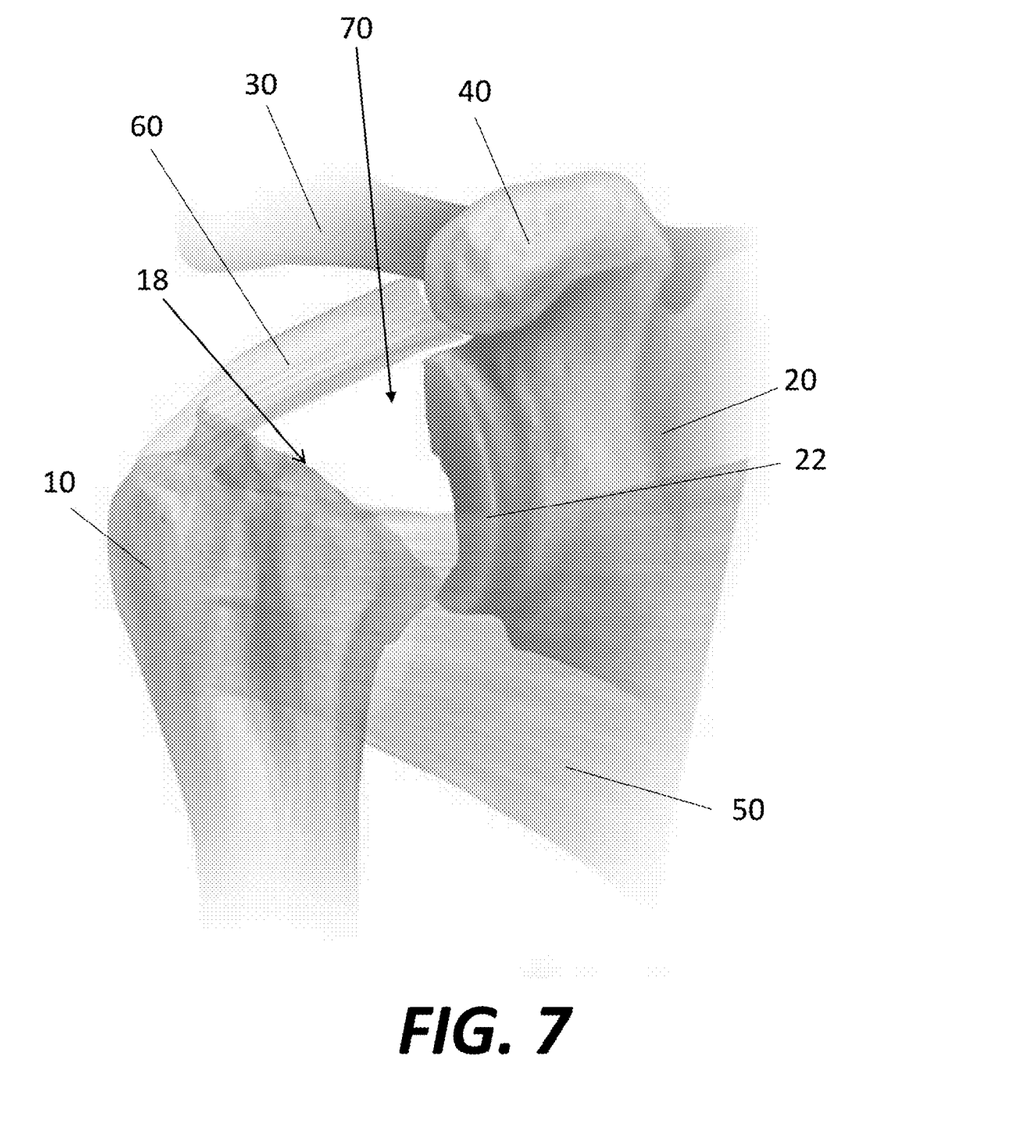
FIG. 7 is illustrates a resected surface of the humeral head of FIG. 6 after the two portions of the humeral head of FIG. 6 have been removed.

FIG. 5 illustrates the shoulder joint after the central segment 12 of the head of humerus 10 has been removed. Following removal of the central segment 12 of the head of humerus 10, the remaining void space 12' may be accessed through the incision and through the rotator cuff interval 70 in order to perform additional resections, for example to complete the removal of the head of humerus 10. As illustrated in FIG. 5, a fourth cut 4 extending substantially parallel to the third cut 3 may be made to remove a lateral segment 14 of the head of the humerus 10, and a fifth cut 5 extending substantially parallel to the third cut 3 may be made to remove a medial segment 16 of the head of the humerus 10. The fourth cut 4 and fifth cut 5 may be performed after inserting a blade or other resection tool into void space 12', so that the cuts can be made without unnecessary damage to surrounding soft tissues. Although the third cut 3, fourth cut 4, and fifth cut 5 are described as being substantially parallel, it should be understood that deviations from parallel are acceptable and the precise contours of the cuts may be dictated by surgeon preference and/or patient anatomy. However, it should be understood that in some cases it may be preferable for the third cut 3, fourth cut 4, and fifth cut 5 to be as close to parallel as possible so that the remaining surface of the proximal humerus 10 is planar or close to planar, which may be desirable for interaction with certain prosthetic implants. The lateral segment 14 and medial segment 16 of the head of humerus 10 may be removed from the patient, for example through the rotator cuff interval 70 and through the incision in the patient as shown in FIG. 6. The remaining resected surface 18 of the head of humerus 10 is illustrated in FIG. 7 after the removal of the lateral segment 14 and medial segment 16 of the head of humerus 10.

It should be understood that any or all of the resections described above may be made manually by a surgeon with a suitable tool such as a reciprocating saw, by a fully autonomous robot equipped with a cutting tool, by a semi-autonomous robot that includes a cutting tool that is at least partially controlled by a surgeon, or by any combination of the above.

Figure 9:
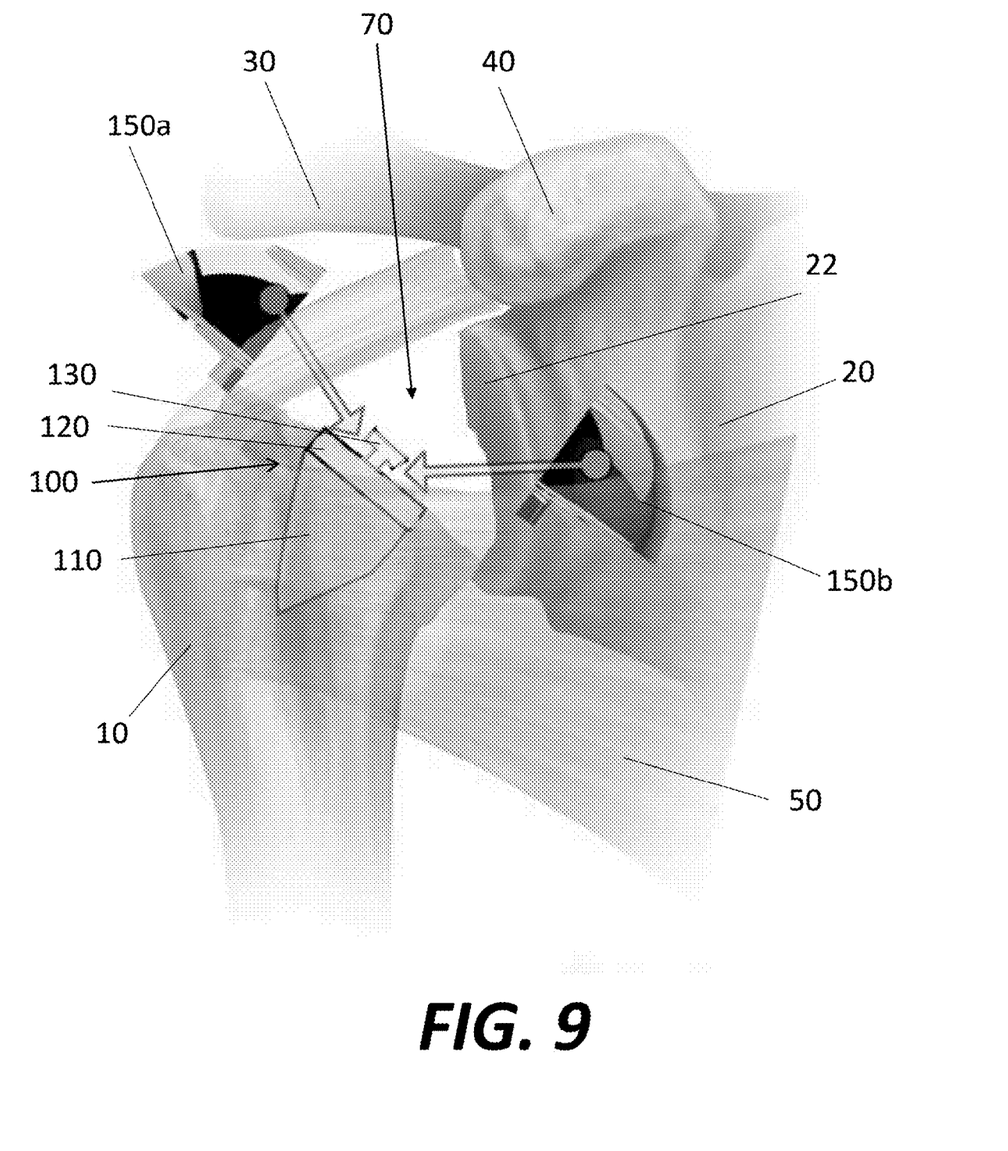
FIGS. 9-10 illustrate two portions of a prosthetic humeral head being implanted.

In a first implantation step, as shown in FIG. 9, a base 100 of a stemless prosthetic humeral head is passed through the incision and through the rotator cuff interval 70 and implanted into the proximal humerus 10.

Base 100 may take any desirable form, but preferably is small enough to pass through the incision and the rotator cuff interval 70 without the need to cut any soft tissue unnecessarily. In the illustrated embodiment, base 100 includes an anchor 110 adapted to anchor into the proximal humerus 10, for example the spongy cancellous portion of humerus 10. The base 100 illustrated in FIG. 8 may also include a collar 120 positioned superior the anchor 110 and adapted to sit approximately flush with the resected surface 18 of the proximal humerus 10. Base 100 may also include a coupling member 130 that is adapted to couple to one or more pieces of a prosthetic humeral head, as will be described in greater detail below.

Figure 8:
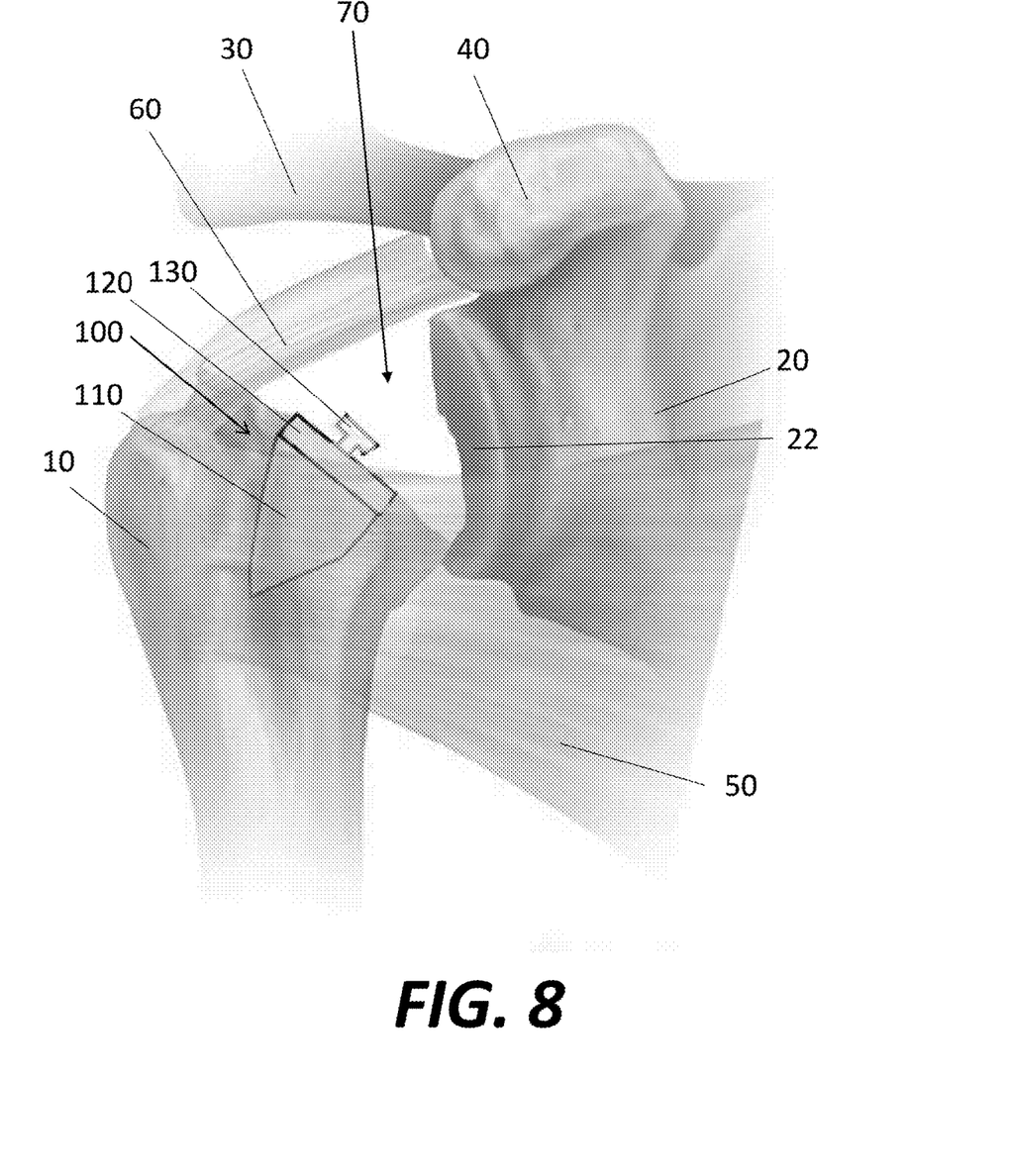
FIG. 8 illustrates a base of a stemless shoulder implant implanted into the resected humeral head of FIG. 7.

Although anchor 110 of base 100 may take any suitable form, preferably anchor 110 includes features that help base 100 strongly affix to the proximal humerus 10 despite the base 100 being stemless. Such features may include flutes and/or roughened surfaces in order to promote bone growth. Various examples of suitable bases are described in greater detail in U.S. patent application Ser. No. 15/926,234, the disclosure of which is hereby incorporated by reference herein. Collar 120 may be substantially circular or cylindrical, although other shapes may be suitable. Preferably, collar 120 includes features to assist in the implantation and/or removal of base 100, such as apertures which allow for screws to pass therethrough or to couple to an insertion tool. Similarly, apertures may be provided in collar 120 to allow for tools to pass through to chip away at bone, which may be useful in a revision procedure in which a previously implanted base 100 needs to be removed. The underside or inferior surface of collar 120 may also include features to assist in securing the base 100 to the proximal humerus, for example pegs or anchors positioned around a circumference or periphery of the collar 120, with the central anchor 110 being positioned radially inward of the smaller pegs or anchors. Those smaller pegs or anchors may include similar features to the anchor 110, such as flutes and/or roughened surfaces.

Coupling member 130, as illustrated in FIG. 8, may take the form of an extension member that extends superior to collar 120, although in other embodiments the coupling member 130 may form a recess, depression, or aperture, such as those shown in U.S. patent application Ser. No. 15/926,234. As shown in FIG. 9, prosthetic humeral head 150 may include two or more parts, such as a lateral portion 150a and a medial portion 150b. When joined together, humeral head 150 may be substantially hemispherical and adapted to simulate the native function of the native humeral head, including articulation within the native glenoid cavity 22 or a prosthetic glenoid cavity. By providing humeral head 150 as two (or more) separate pieces 150a, 150b, the individual pieces may be small enough to insert through the incision and through the rotator cuff interval 70 to couple to the coupling member 130 of the base 100, and also to one another to form the prosthetic humeral head 150. Although FIG. 9 illustrates prosthetic humeral head 150 as two pieces with a lateral member 150a and a medial member 150b that each take the form of substantially half a hemisphere, it should be understood that more than two pieces may be provided if desired, although in all embodiments it is preferable that when the pieces of prosthetic humeral head 150 join together, the prosthetic humeral head is substantially hemispherical. In addition, although prosthetic humeral head 150 is illustrated in FIG. 9 as a lateral member 150a and a medial member 150b, the pieces may be provided as anterior and posterior members or any other desired relative positions.

Figure 10:
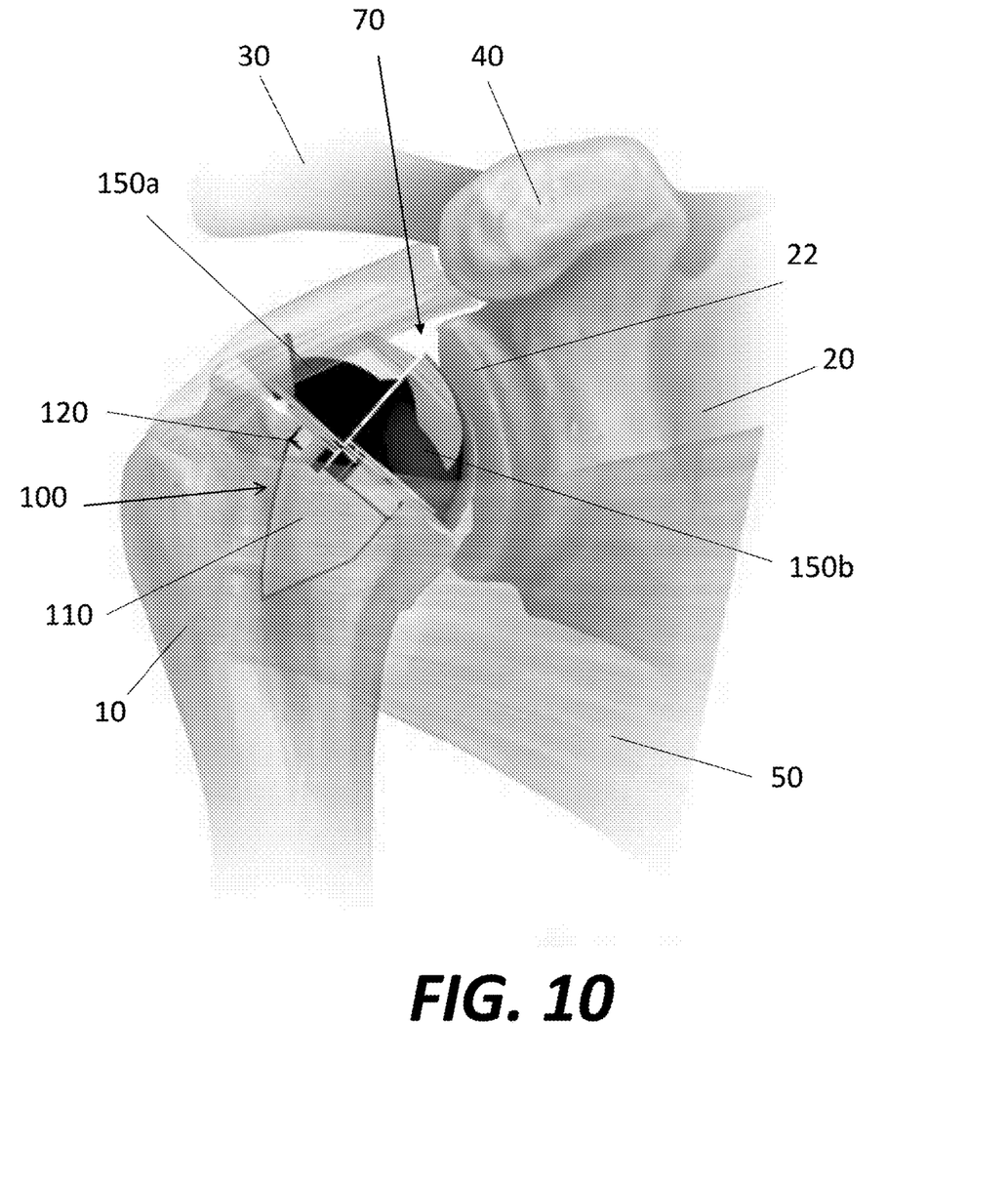
Figure 11:
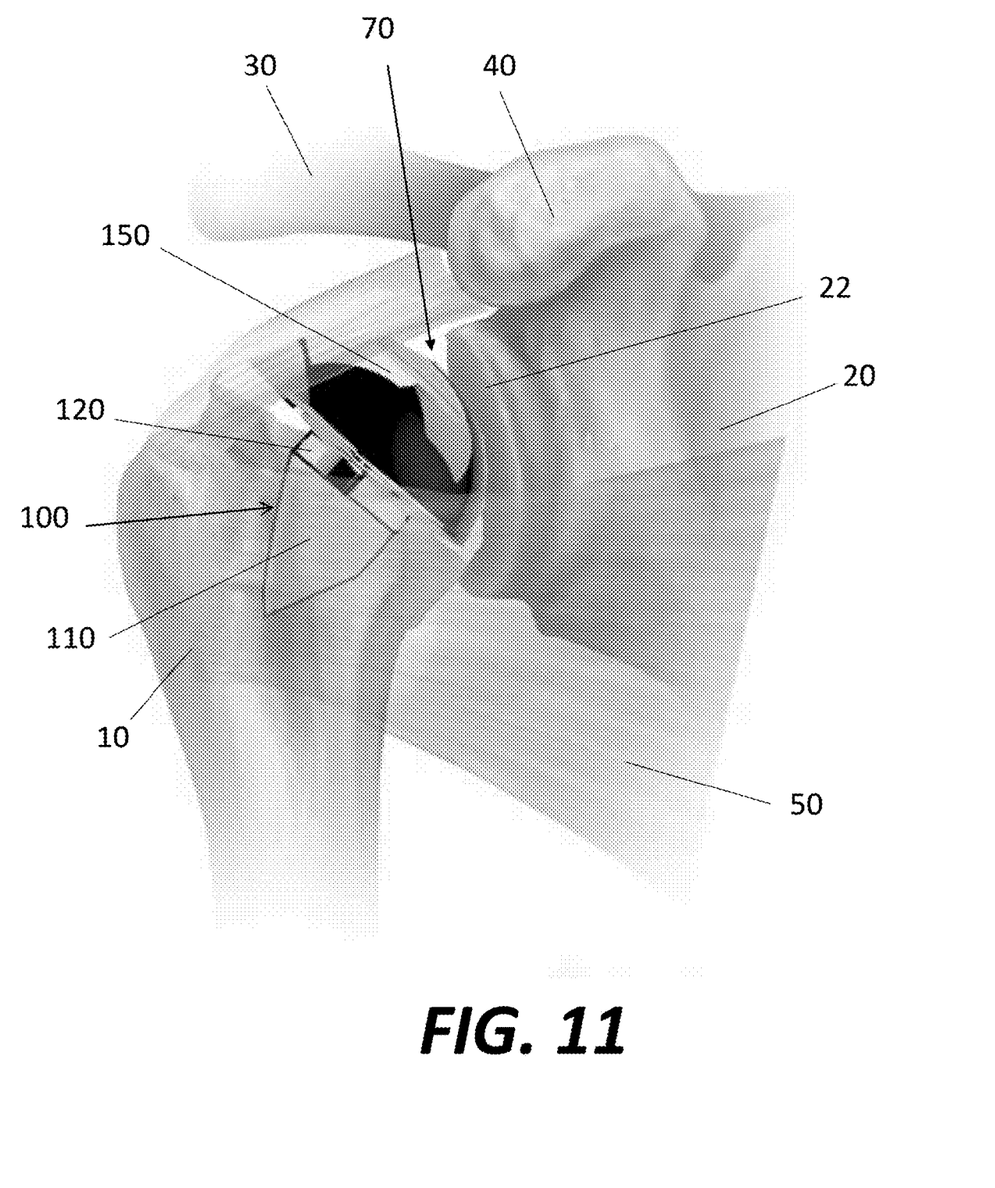
FIG. 11 illustrates the two portions of the prosthetic humeral head having been implanted into the shoulder.

FIG. 10 illustrates the medial portion 150b of prosthetic humeral head 150 having already been coupled to base 100 via coupling member 130, with the lateral portion 150a of prosthetic humeral head 150 being coupled to the coupling member 130 of base 100 and also to the medial portion 150b of the prosthetic humeral head 150. FIG. 11 illustrates the lateral portion 150a of the prosthetic humeral head 150 having been coupled to both base 100 and the lateral portion 150b of the prosthetic humeral head 150, completing the implantation of the prosthetic humeral head 150.

In the embodiment of prosthetic humeral head 150 shown and described in connection with FIGS. 9-11, a gap or seam may result from the coupling of the lateral portion 150a and medial portion 150b of the prosthetic humeral head 150, even though the seam may be small. In some embodiments, it may be preferable to implant prosthetic humeral head 150 so that the seam extends in an anterior-to-posterior direction, as shown in FIG. 10. However, in other embodiments, it may be preferable to implant prosthetic humeral head 150 so that the seam extends in a medial-to-lateral direction, although it should be understood that the prosthetic humeral head 150 may be implanted so that the seam extends in any particular direction. Depending on the size and geometry of the seam, articulation of the prosthetic humeral head 150 against glenoid cavity 22 may cause some amount of irritation. Depending on the particular patient anatomy, a surgeon may choose to implant prosthetic humeral head 150 so that the resulting seam is least likely to cause any problems with that particular patient anatomy. However, it should be understood that the seam of prosthetic humeral head 150 may be small enough or otherwise positioned in a manner to reduce or eliminate any likelihood of problems, such as irritation of tissue against which the prosthetic humeral head 150 articulates.

In other embodiments, the prosthetic humeral head 150 may be provided with features to reduce or eliminate potential issues with the seam. For example, prosthetic humeral head 150 is shown schematically in FIG. 12 implanted into the proximal humerus 10. As shown, the lateral member 150a and medial member 150b are both substantially half hemispherical and coupled to one another and coupling member 130 of base 100. Seam 160 is positioned between the two members 150a, 150b of prosthetic humeral head 150. The majority of the outer surfaces of members 150a, 150b may have a substantially constant radius of curvature. However, the radius of curvature of the outer surfaces may decrease at a point near seam 160, where the two half hemispherical shapes come together. With this decreased radius of curvature, no sharp edges near seam 160 will be present to potentially damage any soft tissue against which the prosthetic humeral head 150 articulates. Rather, only the outer surfaces of members 150a, 150b with the larger constant radius of curvature will be in contact with tissue during articulation, so as to reduce or eliminate the possibility of the seam 160, or surfaces adjacent the seam 160, causing irritation to the patient.

Figure 12:
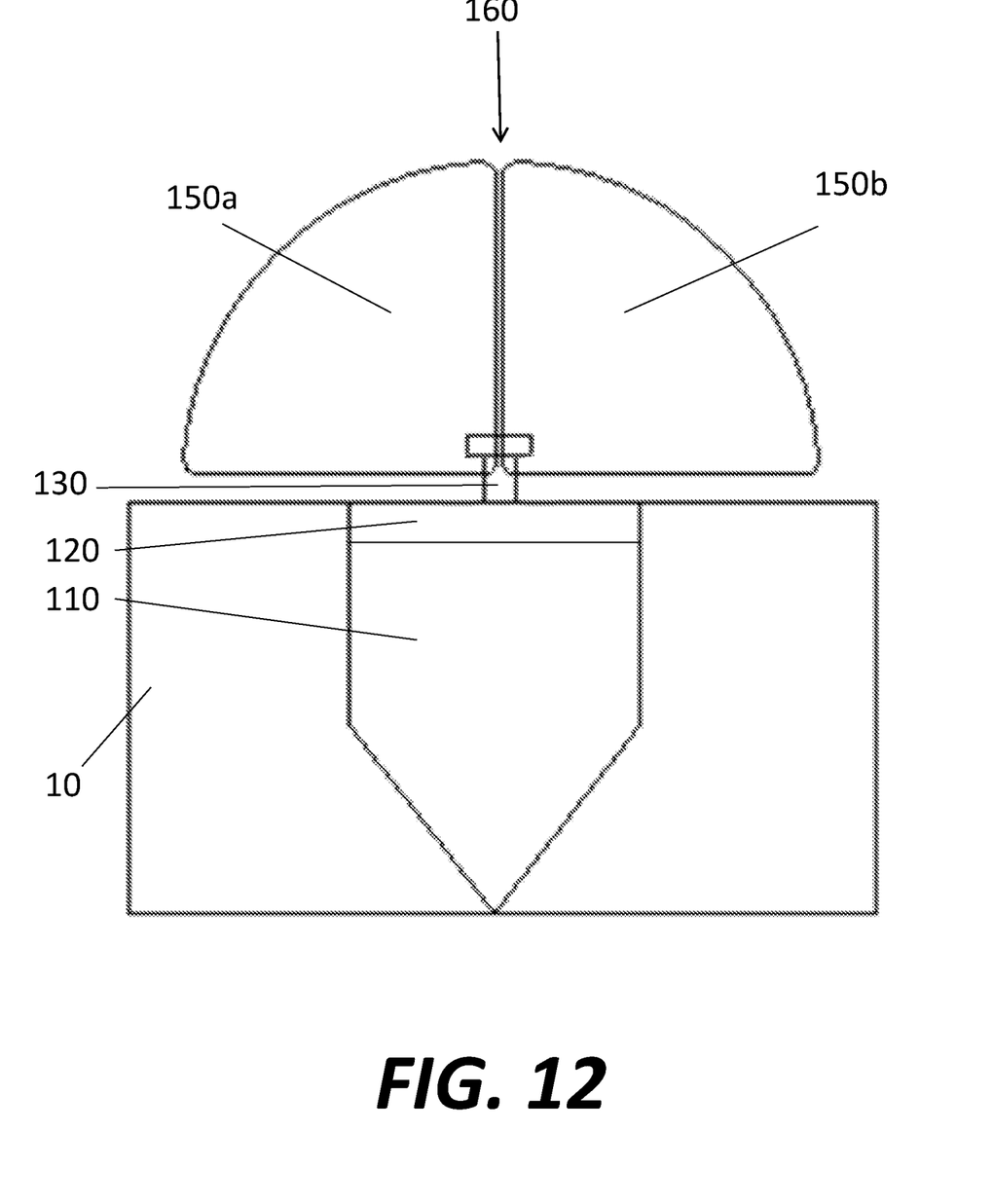
FIG. 12 is a schematic illustration of the stemless prosthetic shoulder implant of FIG. 11 implanted into the proximal humerus.

As noted above, each individual member of prosthetic humeral head 150, such as lateral member 150a and medial member 150b, may lockingly or otherwise couple to base 100, for example to coupling member 130. For example, coupling member 130 may include a relatively narrow post extending superior to collar 120, with a flange or similar feature having a greater width or diameter positioned superior to the narrow post. Each member 150a, 150b may include a corresponding recess to couple to coupling member 130. It should be understood that any locking mechanism may be suitable, such as dovetail shapes, projections that insert into apertures or vice versa, snap-fit features, interference fit features, bayonet connections, etc. While it is preferable that the portions 150a, 150b of prosthetic humeral head 150 may self-lock to base 100, in other embodiments the portions 150a, 150b of prosthetic humeral head 150 may be coupled to base 100 with additional mechanisms, such as screws, adhesives, etc.

In addition to coupling the members 150a, 150b of prosthetic humeral head 150 to base 100, it is also preferable, although not necessarily required, that the members 150a, 150b are coupled to one another upon implantation. As with the coupling of the individual members 150a, 150b to base 100, coupling of the members 150a, 150b to one another may be provided by any suitable mechanism, such as those described above to couple the members 150a, 150b to base 100. For example, member 150a may have a dovetail coupling fit with member 150b, a snap-fit, and/or may be coupled by external mechanisms such as screws or adhesives.

Once the members 150a, 150b of the prosthetic humeral head 150 are coupled to base 100, and to one another, as shown in FIG. 11, the implantation of the prosthetic humeral head 150 is complete. If the glenoid cavity 22 has not been prepared for implantation of a corresponding prosthetic glenoid, that procedure may be completed prior to closing the incision. Otherwise, if the glenoid cavity 22 has already been prepared, or if the glenoid cavity 22 is not intended to be replaced, the incision may be closed and the surgical procedure completed. As noted above, the minimally invasive nature of the method described above requires only a small incision which may result in only a small scar. Further, because the resection of the proximal end of humerus 10, implantation of base 100, and the implantation of prosthetic humeral head 150 can all be completed through the incision and through the rotator cuff interval 70 to spare unnecessary resection or damage of soft tissue. As a result, the patient may be able to begin using the repaired shoulder shortly after completion of surgery, requiring significantly less time of shoulder immobilization as required from traditional shoulder arthroplasty procedures.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A method of implanting a prosthetic stemless shoulder implant comprising:
   making an incision into a shoulder area of a patient;
   inserting a first cutting instrument through the incision and through a rotator cuff interval of the patient;
   resecting a central portion of a native humeral head of the patient with the first cutting instrument;
   removing the central portion of the native humeral head of the patient so that a central void remains where the central portion of the native humeral head was previously positioned;
   inserting a second cutting instrument through the incision, through the rotator cuff interval, and into the central void;
   resecting a medial portion of the native humeral head adjacent the central void;
   removing the medial portion of the native humeral head from the patient;
   resecting a lateral portion of the native humeral head adjacent the central void;
   removing the lateral portion of the native humeral head from the patient;
   implanting a base of a prosthetic stemless shoulder into a proximal portion of the humerus after passing the base through the rotator cuff interval;
   coupling a first portion of a prosthetic humeral head to the base after passing the first portion of the prosthetic humeral head through the rotator cuff interval; and
   coupling a second portion of the prosthetic humeral head to the base and to the first portion of the prosthetic humeral head after passing the second portion of the prosthetic humeral head through the rotator cuff interval, wherein resecting the medial portion of the native humeral head and resecting the lateral portion of the humeral head occurs after the central portion of the native humeral head is resected and removed from the patient.

2. The method of claim 1, wherein the second cutting instrument is the first cutting instrument.

3. The method of claim 1, wherein the prosthetic stemless shoulder implant is implanted without transecting a subscapularis muscle of the patient.

4. The method of claim 1, wherein the prosthetic stemless shoulder implant is implanted without transecting a supraspinatus muscle of the patient.

5. The method of claim 1, wherein resecting the central portion of the native humeral head includes making a first cut in the native humeral head, making a second cut in the native humeral head, and making a third cut in the native humeral head connecting the first cut to the second cut.

6. The method of claim 5, wherein the first cut and the second cut are substantially parallel to one another.

7. The method of claim 6, wherein the third cut is substantially orthogonal to the first cut and to the second cut.

8. The method of claim 5, wherein resecting the medial portion of the native humeral head includes making a fourth cut substantially parallel to the third cut.

9. The method of claim 8, wherein resecting the lateral portion of the native humeral head includes making a fifth cut substantially parallel to the third cut.

10. The method of claim 1, wherein the first cutting instrument is coupled to a robotic surgical system during resection of the central portion of the native humeral head.

11. The method of claim 1, wherein the first cutting instrument is a manual cutting instrument.

12. The method of claim 1, wherein the first portion of the prosthetic humeral head and the second portion of the prosthetic humeral head form a substantially hemispherical shape when coupled together.

13. The method of claim 12, wherein the first portion of the prosthetic humeral head forms a substantially half-hemispherical shape, and the second portion of the prosthetic humeral head forms a substantially half-hemispherical shape.

14. The method of claim 13, wherein a seam is formed between the first portion of the prosthetic humeral head and the second portion of the prosthetic humeral head when the first portion of the prosthetic humeral head is coupled to the second portion of the prosthetic humeral head.

15. The method of claim 14, wherein the first portion of the prosthetic humeral head has an outer surface with a substantially constant first radius of curvature and a region adjacent the seam having a second radius of curvature smaller than the first radius of curvature.

16. The method of claim 1, wherein the first portion of the prosthetic humeral head is coupled to the base prior to coupling the second portion of the prosthetic humeral head to the first portion of the prosthetic humeral head.

\* \* \* \* \*